United States Patent [19]
Fangrow, Jr. et al.

[11] Patent Number: 5,810,792
[45] Date of Patent: Sep. 22, 1998

[54] LOCKING BLUNT CANNULA

[75] Inventors: Thomas F. Fangrow, Jr., Mission Viejo; Daniel J. Wait, Santa Ana; George A. Lopez, Laguna Beach; David Charles Arnold, Mission Viejo; Dennis M. Bui, Alta Loma; Kevin Barry Hanly, Mission Viejo, all of Calif.

[73] Assignee: ICU Medical, Inc., San Clemente, Calif.

[21] Appl. No.: 627,881

[22] Filed: Apr. 3, 1996

[51] Int. Cl.[6] ................................................. A61M 25/00
[52] U.S. Cl. ................................................................ 604/283
[58] Field of Search .................................... D24/112, 129, D24/130; 604/280, 283, 905, 403, 411; 285/81, 82, 91, 92, 386, 387

[56] References Cited

U.S. PATENT DOCUMENTS

| | | |
|---|---|---|
| D. 321,250 | 10/1991 | Jepson et al. . |
| D. 321,251 | 10/1991 | Jepson et al. . |
| D. 321,252 | 10/1991 | Jepson et al. . |
| D. 327,318 | 6/1992 | Dudar et al. . |
| 1,578,517 | 3/1926 | Hein . |
| 2,210,098 | 8/1940 | Ravenscroft . |
| 2,230,098 | 1/1941 | Wurzburger . |
| 2,289,677 | 7/1942 | Perelson . |
| 2,847,995 | 8/1958 | Adams . |
| 2,999,499 | 9/1961 | Willet . |
| 3,134,380 | 5/1964 | Armao . |
| 3,354,881 | 11/1967 | Bloch . |
| 3,502,097 | 3/1970 | Muller . |
| 3,583,391 | 6/1971 | Cox et al. . |
| 3,630,199 | 12/1971 | Gangarosa et al. . |
| 3,648,684 | 3/1972 | Barnwell et al. . |
| 3,797,486 | 3/1974 | Shaps . |
| 3,861,388 | 1/1975 | Vaughn . |
| 3,974,832 | 8/1976 | Kruck . |
| 3,976,063 | 8/1976 | Henneman et al. . |
| 3,976,073 | 8/1976 | Quick et al. . |
| 3,986,508 | 10/1976 | Barrington . |
| 3,993,063 | 11/1976 | Larrabee . |
| 3,994,293 | 11/1976 | Ferro . |
| 4,005,710 | 2/1977 | Zeddies et al. . |
| 4,019,512 | 4/1977 | Tenczar . |
| 4,040,420 | 8/1977 | Speer . |
| 4,076,285 | 2/1978 | Martinez . |
| 4,080,965 | 3/1978 | Phillips . |
| 4,121,585 | 10/1978 | Becker, Jr. . |
| 4,128,098 | 12/1978 | Bloom et al. . |
| 4,149,535 | 4/1979 | Volder . |
| 4,161,949 | 7/1979 | Thanawalla . |
| 4,187,846 | 2/1980 | Lolachi et al. . |
| 4,191,183 | 3/1980 | Mendelson . |
| 4,214,779 | 7/1980 | Losell . |

(List continued on next page.)

FOREIGN PATENT DOCUMENTS

| | | |
|---|---|---|
| 1105959 | 7/1981 | Canada . |
| 0114677 A2 | 1/1984 | European Pat. Off. . |
| 0237321 A2 | 9/1987 | European Pat. Off. . |
| 0240987 A2 | 10/1987 | European Pat. Off. . |
| 0309771 A1 | 4/1989 | European Pat. Off. . |
| 0453264A1 | 10/1991 | European Pat. Off. . |
| 0459812A1 | 12/1991 | European Pat. Off. . |
| 2364655 | 9/1976 | France . |
| 855319 | 7/1949 | Germany . |
| 1166416 | 3/1964 | Germany . |
| G 84 25 197.2 | 9/1985 | Germany . |
| 9013145 | 11/1990 | Germany . |
| 01146777 | 8/1985 | WIPO . |
| WO 86/01712 | 3/1986 | WIPO . |
| WO 86/03416 | 6/1986 | WIPO . |

*Primary Examiner*—Manuel Mendez
*Attorney, Agent, or Firm*—Knobbe, Martens, Olson & Bear LLP

[57] ABSTRACT

Disclosed is a medical connector for introducing medication to a patient in a safe, convenient way by releasably locking an influent fluid line to a receiving port, and method of manufacturing the same. The connector comprises a cannula recessed within a cavity defined by a housing. The housing contains a retaining ridge and gripping members to prevent accidental disconnection of the connector for the port.

20 Claims, 8 Drawing Sheets

U.S. PATENT DOCUMENTS

| | | |
|---|---|---|
| 4,219,912 | 9/1980 | Adams . |
| 4,232,669 | 11/1980 | Nitshke . |
| 4,257,416 | 3/1981 | Prager . |
| 4,265,280 | 5/1981 | Ammann et al. . |
| 4,294,249 | 10/1981 | Sheehan et al. . |
| 4,296,949 | 10/1981 | Muetterties et al. . |
| 4,306,705 | 12/1981 | Svensson . |
| 4,327,726 | 5/1982 | Kwong et al. . |
| 4,328,802 | 5/1982 | Curley et al. . |
| 4,329,987 | 5/1982 | Rogers et al. . |
| 4,334,551 | 6/1982 | Pfister . |
| 4,338,933 | 7/1982 | Bayard et al. . |
| 4,340,097 | 7/1982 | Ammann et al. . |
| 4,340,148 | 7/1982 | Beckham . |
| 4,362,156 | 12/1982 | Feller, Jr. et al. . |
| 4,392,499 | 7/1983 | Towse . |
| 4,405,163 | 9/1983 | Voges et al. . |
| 4,411,662 | 10/1983 | Pearson . |
| 4,413,992 | 11/1983 | Soika . |
| 4,432,759 | 2/1984 | Gross et al. . |
| 4,432,765 | 2/1984 | Oscarsson . |
| 4,439,188 | 3/1984 | Dennehey et al. . |
| 4,439,193 | 3/1984 | Larkin . |
| 4,440,207 | 4/1984 | Genatempo et al. . |
| 4,447,230 | 5/1984 | Gula et al. . |
| 4,452,473 | 6/1984 | Ruschke . |
| 4,457,749 | 7/1984 | Bellotti et al. . |
| 4,496,352 | 1/1985 | Soika . |
| 4,508,367 | 4/1985 | Oreopoulos et al. . |
| 4,511,359 | 4/1985 | Vaillancourt . |
| 4,512,766 | 4/1985 | Vaillancourt . |
| 4,564,054 | 1/1986 | Gustavsson . |
| 4,573,974 | 3/1986 | Ruschke . |
| 4,607,868 | 8/1986 | Harvey et al. . |
| 4,617,012 | 10/1986 | Vaillancourt . |
| 4,639,019 | 1/1987 | Mittleman . |
| 4,645,494 | 2/1987 | Lee et al. . |
| 4,655,753 | 4/1987 | Bellotti et al. . |
| 4,673,400 | 6/1987 | Martin . |
| 4,706,487 | 11/1987 | Bandou et al. . |
| 4,725,267 | 2/1988 | Vaillancourt . |
| 4,752,292 | 6/1988 | Lopez et al. ............................. 604/244 |
| 4,767,412 | 8/1988 | Hymanson . |
| 4,775,369 | 10/1988 | Schwartz . |
| 4,781,702 | 11/1988 | Herrli . |
| 4,784,650 | 11/1988 | Coburn . |
| 4,790,832 | 12/1988 | Lopez . |
| 4,810,241 | 3/1989 | Rogers . |
| 4,834,716 | 5/1989 | Ogle, II . |
| 4,846,809 | 7/1989 | Sims . |
| 4,874,377 | 10/1989 | Newgard et al. . |
| 4,878,897 | 11/1989 | Katzin . |
| 4,880,414 | 11/1989 | Whipple . |
| 4,889,527 | 12/1989 | Herrli . |
| 4,895,562 | 1/1990 | Lopez . |
| 4,946,455 | 8/1990 | Rosen ...................................... 604/403 |
| 4,998,927 | 3/1991 | Vaillancourt . |
| 5,024,616 | 6/1991 | Ogle, II . |
| 5,065,783 | 11/1991 | Ogle, II . |
| 5,120,324 | 6/1992 | Sancoff ................................... 604/283 |
| 5,137,524 | 8/1992 | Lynn et al. ............................. 604/283 |
| 5,167,642 | 12/1992 | Fowles . |
| 5,192,273 | 3/1993 | Bierman et al. ....................... 604/174 |

LOCKING BLUNT CANNULA

BACKGROUND OF THE INVENTION

1. Field of the Invention

This invention relates generally to medical connectors used in the treatment of the injured or sick, and in particular to a connector for introducing medication into a patient in a safe, convenient way.

2. Background Discussion

It is a common practice in treating patients, particularly patients who must be cared for under emergency conditions, to introduce medication into the patient intravenously. An intravenous solution, commonly referred to as parenteral liquid, is fed from a container holding this liquid. The liquid flows through tubing into a needle or catheter which has been inserted into the patient's vein. The catheter is taped securely to the patient's body and is not likely to pull loose if the patient moves. Medication needed to sustain the life of the patient, for example, drugs which maintain the blood pressure of the patient at the desired level, are added to the parenteral liquid. The conventional practice is to introduce the medication through a second conduit in communication with a sealed entry port in the tubing through which the parenteral liquid flows.

It is also common to use a connector to place the second conduit in connection with the conduit carrying the parenteral liquid to avoid the problems of accidental removal, needle sticks, and contamination. FIG. 8 shows one such connector, which has a cannula at one end for insertion into a sealed entry port that leads to the patient's vein, and a luer lock at the other end for securing the connector to the influent fluid line or second conduit. To lock the connector to the entry port, a pair of grip elements are provided. The grip elements have a pair of handles that operate the snap-on grips. The snap-on grip elements secure the connector to the sealed entry port. The entry port has a larger outer diameter than the tubing, thereby providing an edge of a relatively small depth. By releasing the handles, the grips snap on the edge of the entry port so that the connector cannot be easily pulled apart from the entry port. The movement of the handles and grips is within an X-Y plane defined by the handles and grips in two dimensions. There are still, however, significant problems with this type of connector.

One problem with this device is that it can be easily knocked loose from the entry port in a direction substantially transverse to the X-Y plane defined by the pair of grips and handles. Although the snap-on mechanism makes it easy to connect and disconnect the fluid lines, it can only resist forces that are in the general direction of the X-Y plane defined by the grips and handles. Forces in other directions that are not substantially parallel to that X-Y plane can disengage the snap-on grips because the grips provide little resistance in those directions. Such accidental removal of the connector from the sealed port can have very serious consequences and even lead to the death of the patient.

Another problem with the connector in FIG. 8 is infection. All too often a patient's life is seriously endangered by bacteria gaining entry into a patient's bloodstream and infecting the patient. In a vast number of cases it is unknown how the bacteria gain entry. One likely way the bacteria gain entry is by contamination of the cannula that is inserted into the sealed entry port. This happens when the nurse notices that the connector has been pulled loose and simply reinserts it, even though the cannula may contain bacteria on its surface due to direct contact with, for example, the patient's bedding.

SUMMARY OF THE INVENTION

The problems discussed above present a serious health hazard to patients and their nurses. The present invention eliminates these problems and provides a medical connector which is both safe and convenient to use.

There are several features of this invention which contribute to its safety and convenience, no single one of which is solely responsible for these desirable attributes. Without limiting the scope of this invention as expressed by the claims, its more prominent features will now be discussed briefly. After considering this discussion, and particularly after reading the section of the application entitled "Detailed Description of the Preferred Embodiments," one will understand how the features of this invention provide the attributes of safety and convenience.

One feature of this invention is the use of a housing to enclose the cannula that is to be inserted into the sealed entry port structure. This housing fits snugly over the entry port structure, cooperating with the port structure in a male-female mating relationship. The cannula penetrates the seal when the housing is coupled with the port structure. This cannula is recessed within a cavity in the housing which terminates with an open mouth into which the sealed end of the port structure fits. Commonly, such a port structure is referred to as a Y-site or piggyback connector. Since the cannula is disposed within the housing, the likelihood of bacteria contamination, touch contamination, and injuries to healthcare workers due to piercing element sticks are avoided or reduced.

A second safety feature of this invention is that the housing has a wall structure which substantially encircles the sealed entry port structure. A locking mechanism which releasably secures the connector to the port structure forms part of the housing wall structure. The housing ensures that the connector can be removed from the entry port only by pulling it in the direction along the longitudinal axis of the housing. A force on the connector in a direction substantially transverse to its longitudinal axis will not easily knock loose and disconnect the connector. Because of this feature, movement of the patient does not result in accidental removal of the cannula from the seal.

The preferred embodiment of the invention illustrating all of the features of this invention will now be discussed in detail. This invention may be used to administer medication to a patient intravenously, intracranially, or intraperitoneally.

BRIEF DESCRIPTION OF THE DRAWING

The drawing depicts the preferred embodiment of this invention in which.

DETAILED DESCRIPTION OF THE PREFERRED EMBODIMENTS

A. Prior Art

Figure 8:
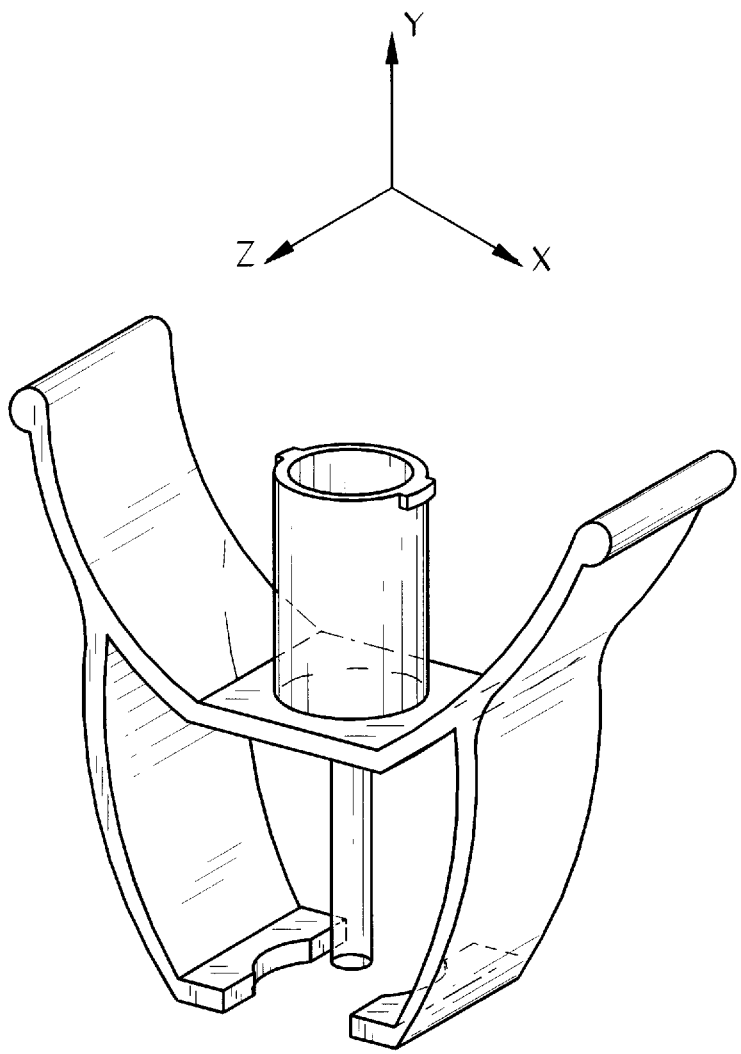
FIG. 8 is a perspective view of a prior art medical connector.

As shown in FIG. 8, the existing connector mates with an influent fluid line via a receiving port (not shown) and allows fluid to flow through the cannula which penetrates a sealed entry port. The two arms on opposite sides of the cannula form a locking mechanism that includes two grip handles and two snap-on grips. The grips fit over the edge of the entry port, and lock the connector in place to prevent the influent fluid line and entry port from being disconnected. The locking mechanism defines an X-Y plane and operates essentially in that plane as the handles are manipulated to move the grips over the edge of the entry port. The connector is secured to the entry port by the grips, but resists only those forces that are substantially in the X-Y plane, including the direction of pulling the connector out of the entry port along the Y-axis. Forces that are not substantially in the X-Y plane, especially those that are substantially transverse to the X-Y plane, such as along the Z-axis, can dislodge the connector from the entry port with ease. When that occurs, the flow of medication is disrupted endangering the patient, and the consequences can be fatal.

In addition to the problem of accidental disconnection, the cannula is exposed to the surroundings and can easily be contaminated either before it is first inserted into the entry port or when it is accidentally disconnected from the entry port. The nurse's hands may touch the cannula and contaminate it, or the cannula may contact the floor or the patient's bedding and contact bacteria. This bacteria may travel into the patient's bloodstream.

These problems associated with the existing practice are eliminated by the preferred embodiment of this invention disclosed hereinafter.

B. Preferred Embodiment of the Invention

Figure 1:
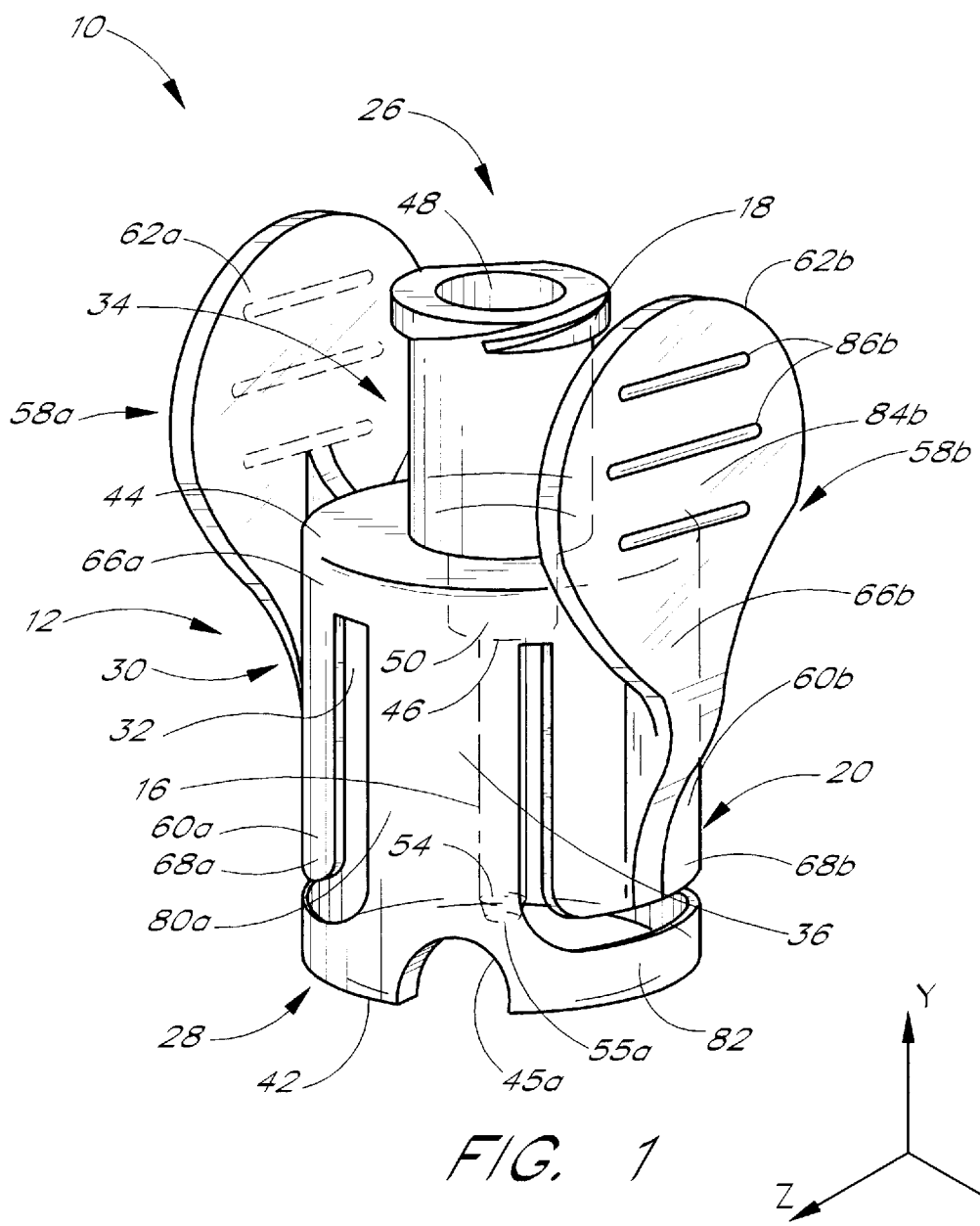
FIG. 1 is a perspective view of the preferred embodiment of the connector of the present invention, which employs a pair of locking grips for securing the housing to the port structure.

FIGS. 1–6 illustrate a preferred embodiment of the present invention. Referring to FIG. 1, a connector 10 is provided which employs a housing 12 which surrounds a luer or cannula 16 recessed within the housing 12 to protect it from contamination from contact with a nurse's hand or a patient's bedding or other such surfaces if the connector 10 is accidentally dropped. The connector 10 preferably has a luer lock 18 at one end for attachment to an influent fluid line (not shown) and a grip mechanism 20 near the other end to secure the connector 10 to an entry port (not shown).

1. Housing

The housing 12 preferably has a proximal end 26 and a distal end 28 and is defined by a wall structure 30. The wall structure 30 forms an internal cavity 32 with a head portion 34 adjacent the proximal end 26, and a body portion 36 adjacent the distal end 28. The wall structure 30 of the head portion 34 defines a first opening 40 at the proximal end 26 which is dimensioned to cooperate with the influent line. At the distal end 28 of the housing 12, the wall structure 30 of the body portion 36 defines a second opening 42 sufficiently large to fit over the entry port (not shown). An annular portion 44 divides the head portion 34 and the body portion 36.

In the preferred embodiment, the head portion 34 and body portion 36 are of cylindrical shape and the wall structure 30 may have a substantially uniform thickness. The body portion 36 is desirably cylindrical in shape with an inner diameter slighter larger than the outer diameter of the entry port. The annular portion 44 is desirably an annular circular disk with an outer diameter equal to the outer diameter of the body portion 36 and an inner diameter equal to or smaller than the inner diameter of the head portion 34.

When assembled, the entry port is enwrapped by the body portion 36 as will be easily understood by those of skill in the art. The longitudinal axis of the housing 12 coincides with the axis of the head portion 34 and the axis of the body portion 36, and is parallel to the Y-axis as illustrated in FIG. 1. The body portion 36 may have a larger diameter than the head portion 34 as in the preferred embodiment illustrated in FIGS. 1–6.

Figure 3:
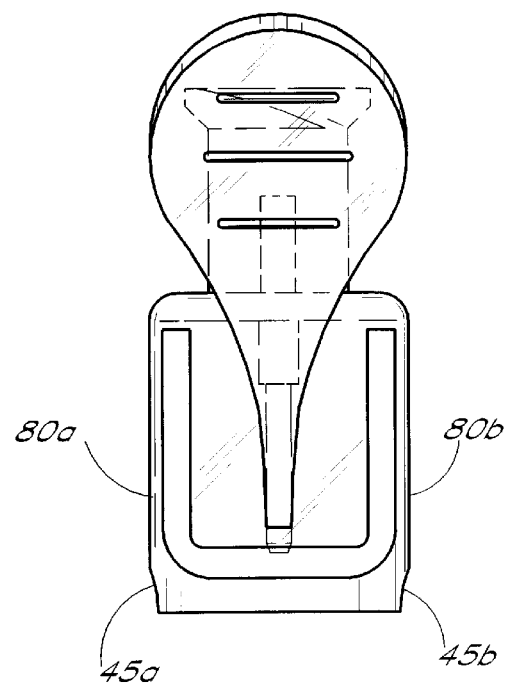
FIG. 3 is a right side elevational view of the connector shown in FIG. 1.
Figure 4:
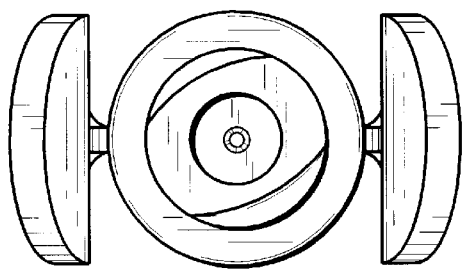
FIG. 4 is a top plan view of the connector shown in FIG. 1.
Figure 5:
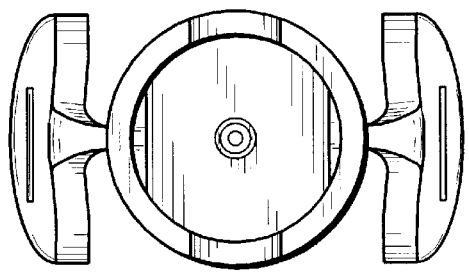
FIG. 5 is a bottom plan view of the connector shown in FIG. 1.

As best shown in FIGS. 1 and 3, desirably two scoops are provided, a first scoop 45*a* cut out from the wall structure 30 at the distal end 28 of the housing 12, and a second scoop 45*b* (FIG. 3) cut out from the wall structure 30 also at the distal end 28. The scoops 45*a* and 45*b* are advantageously on directly opposite sides of the housing 12. The scoops 45*a*, 45*b* are useful when the entry port has a T-shaped or angled entry into a main tube. For such an entry port, a connector without scoops may not be able to engage the edge of the entry port because its distal end may be interfered by the main line. The scoops 45*a* and 45*b* facilitate cooperation between the connector 10 and the main tube and allow the connector 10 to be locked to the entry port without interference from the main tube as will be understood by those of skill in the art. The scoops 45*a* and 45*b* are preferably of semicircular or truncated semicircular shape and of a size that would be suitable for a range of commonly used tubes.

2. Luer Lock

As best seen in FIG. 1, a luer lock 18 is disposed at the proximal end 26 of the head portion 34 of the housing 12. The luer lock 18 allows the connector 10 to be secured to a fluid line without the need for tapes or external attachment mechanisms. The luer lock 18 facilitates quick connection and disconnection with a fluid line which is generally equipped with a luer lock at its end. In the preferred embodiment shown in FIGS. 1–6, the connector 10 has a luer lock 18 with external threads at the proximal end 26 which will mate with a luer lock on the influent fluid line by a simple twist.

It will be apparent to one skilled in the art that other types of locking mechanisms or methods can be employed which are equivalent to the luer lock 18 just described.

3. Cannula

Referring to FIG. 1, a cannula 16 is preferably disposed in the cavity 32 along the longitudinal axis of the housing 12. The cannula 16 is preferably centrally located in the cavity 3*a*. The cannula 16 is preferably made of a plastic, and more preferably polycarbonates. The cannula 16 advantageously has a substantially uniform inner diameter 0.033". Accordingly, the annular portion 44 that defines the division between the head portion 34 and body portion 36 desirably has an inner diameter equal to 0.338".

The proximal end 46 of the cannula 16 advantageously has a scarf or boss 50, which preferably is integrally formed with the cannula 16 and the annular portion 44. The scarf 50 is cylindrical in shape and has an outer diameter larger than that of the cannula 16. The inner diameter of the scarf 50 is desirably equal to 0.033" such that the wall thickness of the scarf 50 is larger than that of the cannula 16. The proximal end 46 of the luer 16 which intersects the annular portion 44 has high stress concentration and is subject to a large bending load when a side force is applied to the distal end 46. This occurs when, for instance, the cannula 16 is penetrating the sealed port. The scarf 50 provides sturdy support for the cannula 16 at its most vulnerable proximal end 46, having the larger wall thickness, and relieves the stress at the proximal end 46, thereby decreasing the stress concentration.

The distal end 54 of the cannula 16 penetrates a seal or septum of the entry port to transfer fluid therethrough. The seal is desirably pre-slit for easy penetration. To further facilitate penetration, the distal end 54 of the cannula 16 desirably has a taper 55.

The entire cannula 16, including the distal end 48, is preferably surrounded by the body portion 36 of the housing 12 in the circumferential direction. Providing the housing 12 to protect the cannula 16 from contamination is a simple yet effective solution to the serious problem of contamination. In addition, the housing 12 assists in solving the problem of accidental disconnection as discussed in detail below.

4. Grip Mechanism

Figure 2:
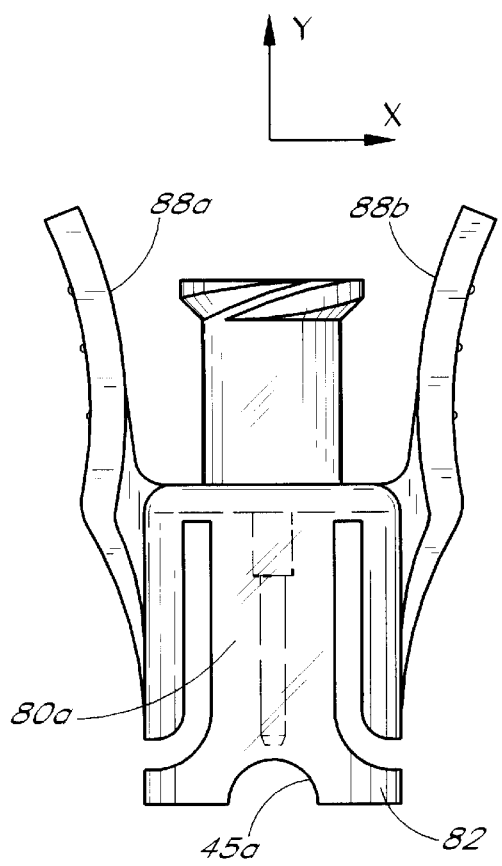
FIG. 2 is a front elevational view of the connector shown in FIG. 1.
Figure 6:
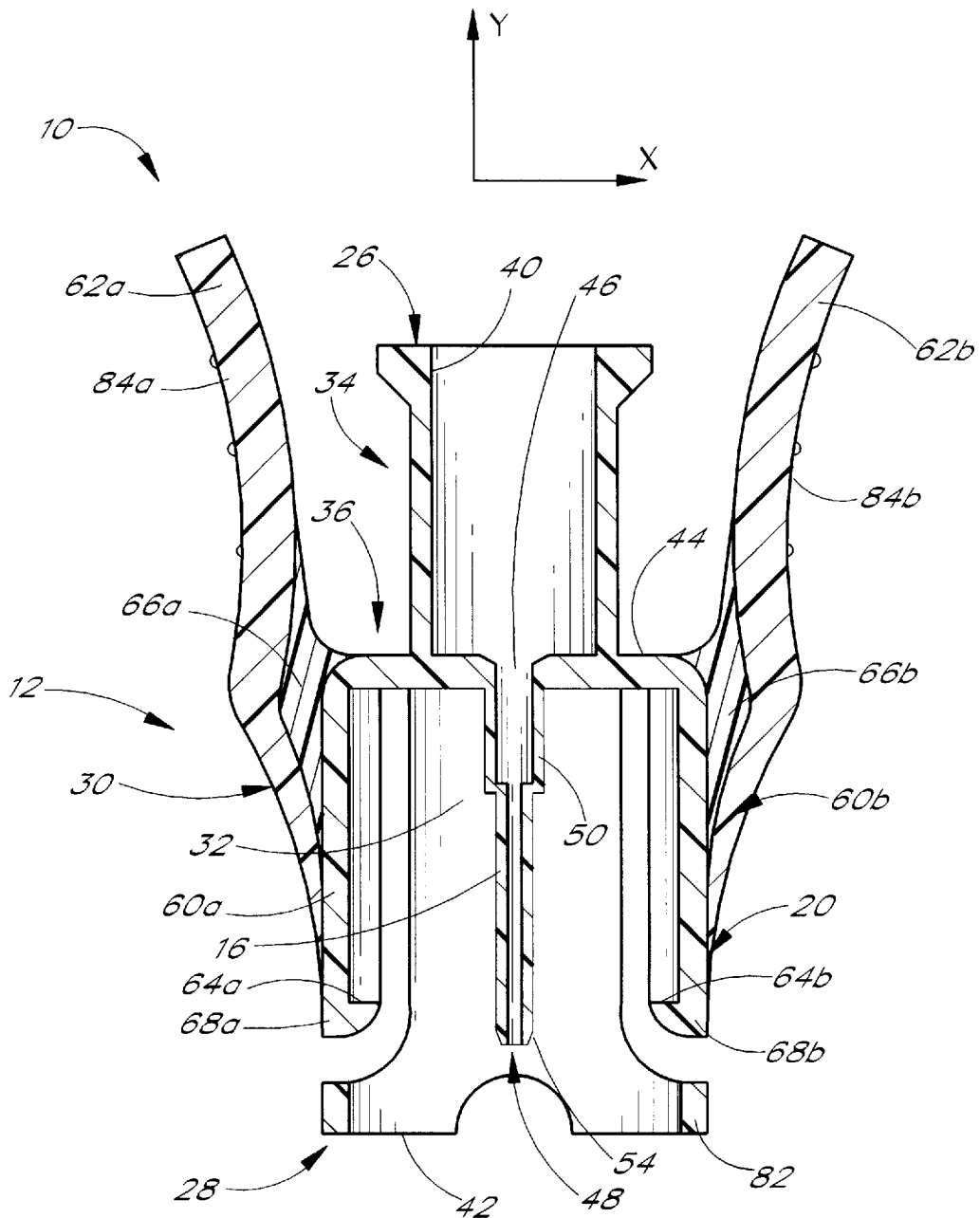
FIG. 6 is a front cross-sectional view of the medical connector shown in FIG. 1.

As best seen in FIGS. 1–2 and 6, the grip mechanism 20 comprises two grip elements 58a and 58b, which include a pair of grips or grip arms 60a and 60b, with handles 62a and 62b, and lips or flanges 64a and 64b. The grip elements 58a and 58b are disposed at the circumference of the body portion 36 of the housing 12, opposite one another and external to the wall structure 30. Each grip 60a/60b has a proximal end 66a/66b and a distal end 68a/68b. Each handle 62a/62b is connected to the proximal end 66a/66b of the grip 60a/60b. At the distal end 68a/68b is the grip flange or lip 64a/64b disposed on the inner surface of the grip 60a/60b. The two grip lips 64a and 64b hence face each other inside the internal cavity 32. The grip elements 58a and 58b are advantageously mirror images of one another.

As best seen in FIGS. 1 and 6, the lip 64a/64b protrudes from the distal end 68a/68b of the grip or grip arm 60a/60b in the cavity 32, and is a flat planar section perpendicular to the longitudinal axis of the body portion 36 and perpendicular to the grip 60a/60b. The lip 64a/64b is advantageously integrally formed with the grips 60a/60b. When both lips 64a and 64b are lodged over an edge or secured inside grooves or depressions of comparable size provided on the entry port, the lips 64a and 64b prevent the connector 10 from being pulled loose by a force substantially in the direction along the longitudinal axis and perpendicular to the planar lips 64a and 64b, as well as a force that is substantially parallel to the X-Y plane defined by the grip elements 58a and 58b. The lips 64a and 64b thus need to have sufficiently large planar area to accomplish that function. The lips 64a and 64b are preferably made of a material that is sufficiently rigid. A hard plastic is preferred, and polycarbonate is most preferred.

In the preferred embodiment, the grips or grip arms 60a and 60b are fixed to the body portion 36, at or near the annular portion 44 of the housing 12. The size and shape of the grips 60a and 60b should be conducive to a certain level of deformation as they are pulled open by operation of the handles 62a and 62b. The grips 60a and 60b need to be sufficiently long in the longitudinal (Y) direction to allow the lips 64a and 64b to be lodged over the edge of the entry port. Each grip 60a/60b is desirably a curved rectangular flap fixed to the body portion 36. The width of the grips 60a and 60b around the circumference of the body portion 36 need not be large, but is preferably not so narrow that the grips 60a and 60b will be subjected to fracture easily, especially in the high stress concentration region along the line of connection between the grips 60a and 60b and the body portion 36 at or near the annular portion 44. But the width cannot be too large or the grip mechanism 20 will not function properly, i.e., it will not be able to pull the grips 60a and 60b apart. Therefore, each of the grips 60a and 60b should span less than 180° around the circumference of the body portion 36. The preferred embodiment in FIGS. 1–6 shows each grip 60a/60b with a width that has approximately a 90° span around the circumference. The span may vary considerably from 90°, depending on the size of the lips 64a and 64b needed. Furthermore, it is understood that the grips 60a and 60b may have other shapes, such as curved, truncated triangles or curved parabolas.

Because the grips 60a and 60b are to be deformed by the handles 62a and 62b, they need to be sufficiently flexible, and yet be adequately resilient to recapture their shapes after repeatedly being pushed apart by the handles 62a and 62b. A tough plastic such as polycarbonate is preferred.

In the preferred embodiment, the grips 60a and 60b form part of the housing wall structure 30 that surrounds the cannula 16 and are integrally formed with the body portion 36. FIGS. 1–6 show side wall portions 80a and 80b disposed opposite one another which, when combined with the grips or flaps 60a and 60b, substantially enclose the cannula 16 around its circumference. There are gaps, advantageously small, between the side wall portions 80a and 80b and the grips 60a and 60b to allow movement of the grips 60a and 60b relative to the side wall portions 80a and 80b without interference therewith.

The side wall portions 80a and 80b meet along the distal end 28 of the housing 12 and surround the distal ends 68a and 68b of the grips 60a and 60b, forming a retaining or retention ring 82 at the distal end 28 of the housing 12. The retaining ring 82 completely enwraps a circumferential region of the cavity 32 adjacent the distal end 28, and is desirably disposed adjacent the side wall portion 80a and 80b. In the preferred embodiment, the scoops 45a and 45b are cut out from the retaining ring 82 near the distal end 28. The thickness of the grips 60a and 60b desirably are substantially uniform, and are the same or substantially the same as the thickness of the wall structure 30 that forms the remaining body portion 36.

The grip handles 62a and 62b have contact surfaces 84a and 84b which are desirably slightly curved to fit the shape of human fingers and to facilitate a better hold and easier manipulation by the fingers. The contact surfaces 84a and 84b are on the concave sides of the grip handles 62a and 62b disposed externally facing away from the housing 12, where human fingers make contact. The contact surfaces 84a and 84b preferably have ridges 86a and 86b which create friction with the fingers for a better grasp. On the convex sides of the grip handles 62a and 62b are inner surfaces 88a and 88b of the handles 62a and 62b. The thickness of the handle 62a/62b is generally uniform. The contact surfaces 84a and 84b of the grip handles 62a and 62b need to be sufficiently large for human fingers and thumbs to manipulate easily, but not so large that they are too big for the fingers or otherwise make the installation of the connector 10 difficult as will be easily understood by those of skill in the art. The contact surfaces 84a and 84b are desirably larger than those provided in the prior art. In the preferred embodiment, the contact surfaces 84a and 84b are of inverted teardrop shape, with the larger rounded portion for human fingers and thumbs to manipulate. It is understood that other suitable shapes can also be used.

As best seen in FIGS. 1–2 and 6, the handles 62a and 62b are connected to the grips 60a and 60b and operate as levers to bend the grips 60a and 60b and open the lips 64a and 64b radially outward from the cavity 32. The fulcrum of the lever is located approximately at the proximal ends 66a and 66b of the grips 60a and 60b, which intersect the annular disc portion 44. In this embodiment, the handles 62a/62b are connected to the grips 60a/60b, and more desirably are integrally formed with the grips 60b/60b. The contact surfaces 84a/84b of the handles 62a/62b need to be disposed at a sufficient distance from the distal ends 68a/68b of the grips 60a/60b, such that human fingers and thumbs can take advantage of and operate the connector 10 with ease. The distance between the contact surfaces 84a/84b and the distal ends 68a/68b in this embodiment may be approximately equal to the length of the housing 12 from the distal end 28 to the proximal end 26.

C. Operation of the Connector

The connector 10 provides several functions in a single structure. Two important functions include (1) having the housing 12 substantially surround the cannula 16 to protect it from accidental contamination and prevent human contact with the cannula, and (2) providing the housing 12 and the retaining ring 82 which substantially enwrap the entry port to prevent accidental disconnection of the connector 10 therefrom. These and other features are explained in the following description of the operation of the connector 10.

The female luer lock 18 of the connector 10 is preferably first attached to the male luer lock provided at the end of an influent fluid line. The next step is to use the index finger and thumb to grasp the contact surfaces 84a and 84b of the grip handles 62a and 62b and press them together. This creates a bending moment, which causes the distal ends 68a and 68b of the grips or flaps 60a and 60b to spread apart. As a result, the grip lips 64a and 64b are pulled apart. The connector 10 is then moved over the entry port to allow it to enter the cavity 32 of the housing 12. The cannula 16 penetrates the seal or septum of the entry port as the housing wall structure 30 guides the entry port into the cavity 32. When the entry port is inside the cavity 32, the handles 62a and 62b are released. The grips 60a and 60b are restored to their undeformed state and the lips 64a and 64b become lodged over the edge of the entry port. The lips 64a and 64b may produce a "click" sound as they are lodged over the edge. The connector 10 is thus releasably secured to the entry port via the lips 64a and 64b. The scoops 45a and 45b allow the connector 10 to be attached to a T-shaped entry port. The connector 10 can be detached from the entry port by pressing the handles 62a and 62b toward each other to disengage the lips 64a and 64b from the edge of the entry port. The connector 10 can then be pulled along its longitudinal axis out of the entry port.

As discussed above, the wall structure 30, formed partially by the grips 60a and 60b and the retaining ring 82, substantially encloses the luer 16 to avoid contamination. The wall structure 30 of the housing 12 serves another significant function aside from that of protecting the cannula 16 from contamination.

The wall structure 30 of the housing 12 also prevents accidental disconnection. As discussed above, the grip lips 64a and 64b work well to prevent the connector 10 from being pulled from the entry port along a direction substantially parallel to the X-Y plane defined by the grip elements 58a and 58b, including the longitudinal axis, because the edge or grooves over which the lips 64a and 64b engage are generally perpendicular to that X-Y plane and the longitudinal axis. But the connector 10 is vulnerable to forces that are substantially perpendicular to the X-Y plane, as the lips 64a and 64b can be dislodged much more readily in those directions. The housing 12 in this embodiment can prevent the connector 10 from being knocked loose in such a way.

As illustrated in FIGS. 1–6, the housing 12 includes side wall portions 80a and 80b which surround the distal ends 68a and 68b of the grips and form a retaining or retention ring 82 at the distal end 28 of the housing 12. When a force substantially perpendicular to the X-Y plane is applied to the connector 10 in the vicinity of its proximal end 26 in the Z-direction, the grip lips 64a and 64b begin to slip out of the edge or grooves provided by the entry port, but the retaining ring 82 near the side walls 80a and 80b bears against the side of the entry port and prevents further tilting of the connector 10 and slipping of the lips 64a and 64b. Indeed, the retaining ring 82 will prevent any forces substantially perpendicular to the longitudinal axis from tilting the connector 10 and disconnecting it from the entry port.

Figure 7:
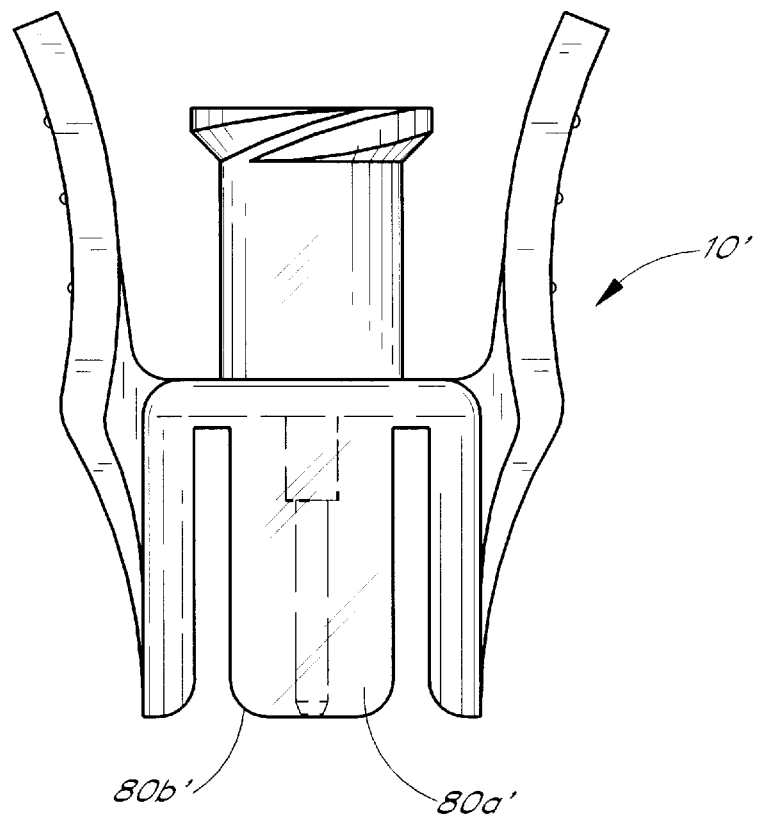
FIG. 7 is a front elevational view of a modified version of the preferred embodiment of the medical connector of the present invention.

The side wall portions 80a and 80b, are preferably snugly fitted over the entry port, which assists in keeping the connector 10 in place, since they will also bear against the side of the entry port under a force in the Z-direction. A connector 10' without the retaining ring is illustrated in FIG. 7. Side wall portions 80a' and 80b' assist in preventing disconnection of the connector 10' and a port (not shown) and assist in preventing contamination as described above. While the side wall portions 80a' and 80b' assist in keeping the connector 10 in place, and may at times function by themselves, a retaining ring 82 (FIG. 1) is preferred.

D. Method of Manufacturing and Processing the Preferred Embodiment

The connector 10 is advantageously a single, integral unit that is molded or cast. It is desirably made of a hard plastic, more desirably a thermoplastic such as polycarbonate. Injection molding is preferred. Any suitable method of injection molding the connector 10 can be utilized.

1. Molding

Figure 9A:
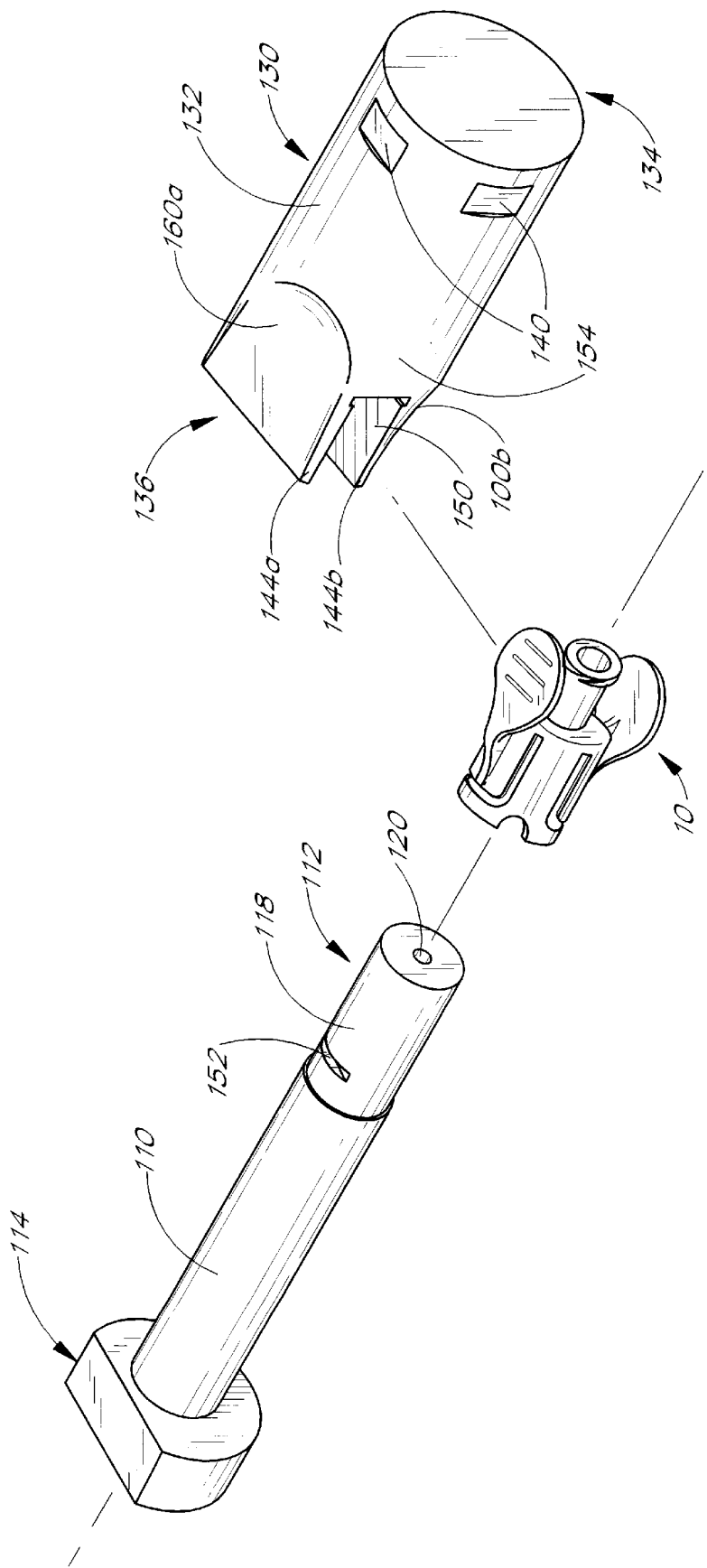
FIG. 9*a* is a blow-up perspective view schematically illustrating a core pin for molding the medical connector of FIG. 1 and the adapter head for removing the connector from the core pin.
Figure 9B:
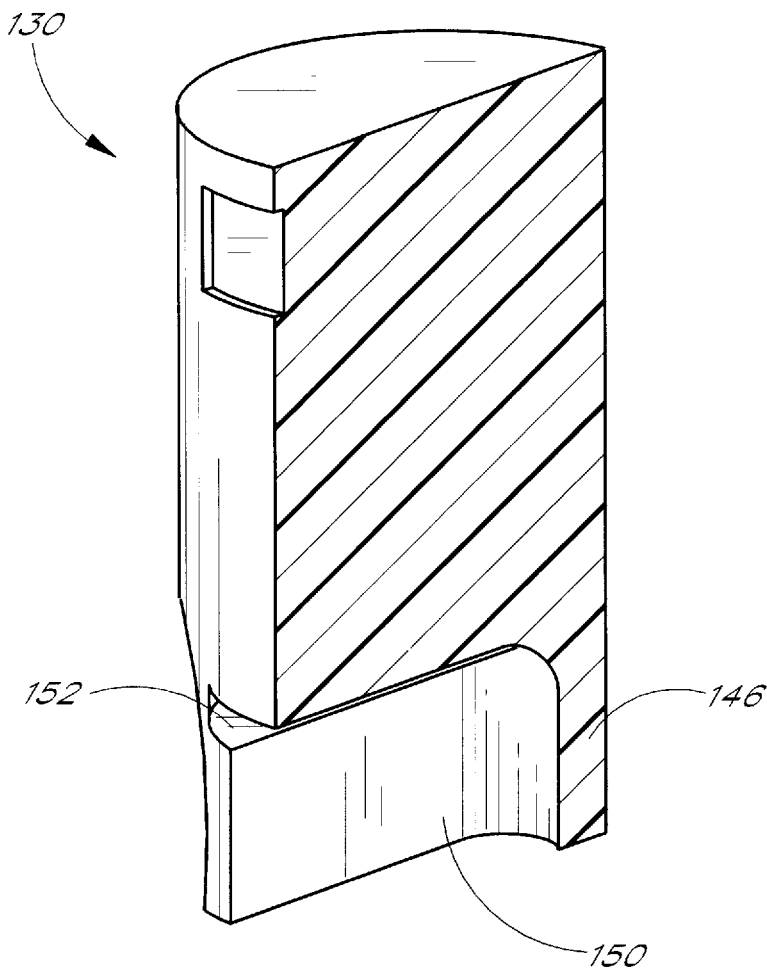
FIG. 9*b* is a different perspective view illustrating the cross-section of the adapter head of FIG. 9*a*.
Figure 9B:
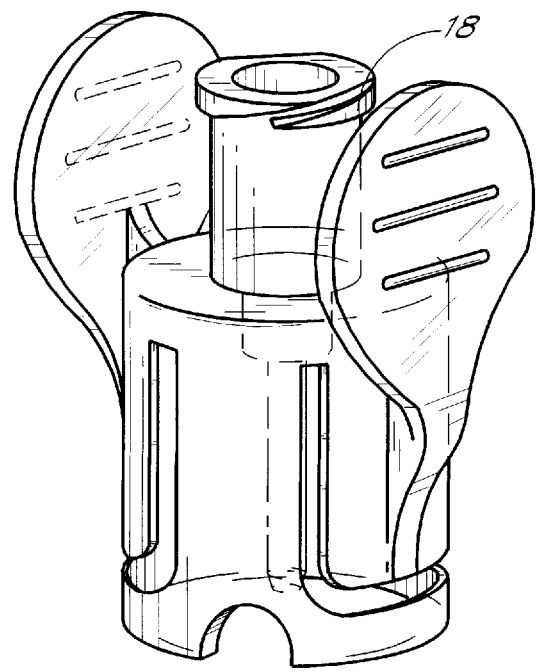
Figure 9B:
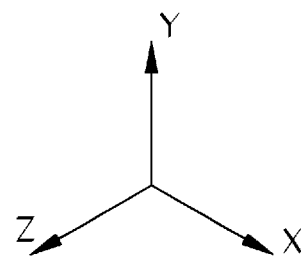
Figure 10:
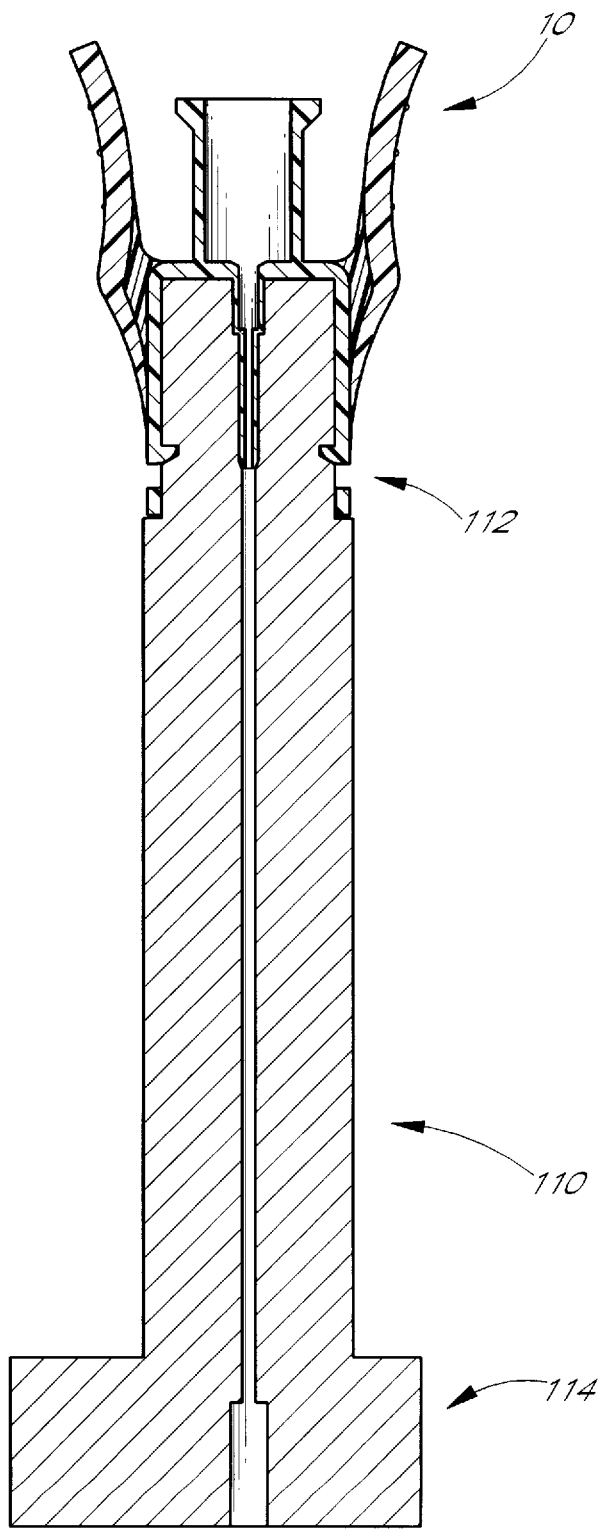
FIG. 10 is a front cross-sectional view of the medical connector of FIG. 1 engaged with the core pin of FIG. 9*a* when the medical connector is molded but not yet removed.

As illustrated in FIGS. 9a, 9b, and 10, injection molding of the preferred embodiment of the connector 10 employs a mold formed by a first core pin 110, a second core pin (not shown), and a pair of slides (not shown). The core pin 110 and the second pin are positioned along an axis with the slides disposed on opposite sides of the pins. A thermoplastic material, preferably polycarbonate, is first softened by heat, and then injected into the mold. The material is allowed to cool and harden in the mold. The slides are pulled away and the second core pin withdrawn without interference with the connector 10, and the connector 10 is then removed from the core pin 110.

The core pin 110 has at one end a mold portion 112 which takes the shape of the internal cavity 32 adjacent the distal end 28 of the connector 10 (FIG. 1). At the other end of the core pin 110 is an attachment portion 114 for attaching the core pin 110 to the injection molding machine (not shown). The mold portion 112 includes a cylindrical body 118 with an inner cavity 120 and a pair of mold grooves 122a and 122b on opposite sides of the cylindrical body 118. The cylindrical body 118 takes the shape of the internal cavity 32 adjacent the distal end 28; the inner cavity 120 takes the shape of the cannula 16; and the mold grooves 122a and 122b are disposed to form the grip lips 64a and 64b.

2. Post-Molding Processing

The method of removing the connector 10 from the core pin 110 is an important feature of the present invention. Generally, when the slides are displaced and the second core pin withdrawn, the molded object can easily be pulled out along the axis of the core pin 110 or be removed by a force or gravity substantially transverse to the axis of the core pin 110. An example is the prior art connector shown in FIG. 8. Just as that connector can easily be knocked loose from an entry port by a force substantially along the Z-axis, it can be removed or can even drop under gravity from the mold portion 112 of the core pin 110 by a force substantially along the Z-axis. In the preferred embodiment, the wall structure 30 which keeps the connector 10 from being knocked off from the entry port also makes it difficult to remove the connector 10 from the mold portion 112 of the core pin 110.

To facilitate quick and easy removal of the connector 10 from the core pin 110 in order to allow the core pin 110 to be remounted for another molding cycle, a tool which employs an adapter head 130 is used. The tool can be either a component of the injection molding apparatus which may be automated, or a manual hand tool having a handle with the adapter head 130 at one end.

Referring to FIG. 9a, the adapter head 130 has a body 132 which desirably has substantially a cylindrical shape. The adapter head 130 comprises a first end 134 and a second end 136. The first end 134 is attached to the tool (not shown). There are a number of flat grooves or sections 140 on the circumferential region of the body 132 near the first end 134. The flat sections 140 provide gripping areas for attachment to the tool to facilitate rotation of the adapter head 130.

The second end 136 is shaped to cooperate with the head portion 34 at the proximal end 26 of the connector 10. As best seen in FIGS. 9a and 9b, the second end 136 comprises two side walls 144a and 144b, and a back wall 146, which together define a cavity 150 that takes generally the external shape of the head portion 34 of the connector 10. The cavity 150 has a groove 152 which matches the external thread protrusion of the male luer lock 18 at the proximal end 26 of the head portion 34 of the connector 10. Preferably, the external surfaces 160a and 160b of the side walls 144a and 144b are shaped to match the inner surfaces 88a and 88b of the grip handles 62a and 62b.

The procedure for removing the connector 10 from the core pin 110 using the adapter head 130 is as follows. The adapter head 130 is positioned with its front side 154 facing the head portion 34 of the connector 10 and the groove 152 aligned with the luer lock 18. The adapter head 130 is moved toward the head portion 34 such that the cavity 150 cooperates with the head portion 34 and the side walls 144a and 144b occupy the space between the head portion 34 and the grip handles 62a and 62b. As the adapter head 130 and the head portion 34 are coupled with one another, the luer lock 18 cooperates with the groove 152 in the cavity 150 and the longitudinal axes of the adapter head 130 and head portion 34 are parallel to one another and desirably coincide. The adapter head 130 is then rotated about its longitudinal axis. This rotation is transferred to the connector 10 because the side walls 144a and 144b are engaged between the head portion 34 and grip handles 62a and 62b. The connector 10 is rotated until the grip lips 64a and 64b are disengaged from the mold grooves 122a and 122b. The turning can be carried out easily because the grip lips 64a and 64b, being flat and parallel to the circumference of the body portion 36, offer little resistance to such rotation. A rotation of about 90° is advantageous since it places the grooves 122a and 122b as far as possible away from the grip lips 64a and 64b. Because the grip lips 64a and 64b are no longer engaged, the connector 10 can slide off the mold portion 112 of the core pin 110. This is accomplished by pulling the adapter head 130 along the longitudinal axis of the connector 10. When the adapter head 130 is pulled, the groove 152 which is coupled with the luer lock 18 engages the luer lock 18 and slides the connector 10 out of the core pin 110 along its axis.

The above description presents the best mode contemplated of carrying out the present invention as depicted by the embodiment disclosed. The combination of features illustrated by the embodiment provide the safety and convenience of this invention. This invention is, however, susceptible to modifications and alternate constructions from the embodiments shown in the drawings and described above. Consequently, it is not the intention to limit the invention to the particular embodiments disclosed. On the contrary, the intention is to cover all modifications and alternate constructions falling within the scope of the invention as generally expressed by the following claims:

What is claimed is:

1. A connector for connecting a fluid line to a port having a receiving end, comprising:

a body having a proximal end and a distal end, said body including a wall structure defining an internal cavity, said distal end having an opening sufficiently large to mate with the receiving end of said port, said cavity being sized to fit snugly on the receiving end of said port, said body having a retaining ring at the distal end thereof;

a hollow spike having a tip and a base, said spike integrally formed with said body of said connector and being attached to said body at said base and seated inside said cavity such that said tip is recessed within said cavity; and a grip mechanism integral with said body to releasably secure the connector onto said port.

2. The connector of claim 1, wherein the body comprises a first cylindrical portion adjacent the proximal end and a second cylindrical portion adjacent the distal end, said first portion being shaped to be placed in fluid communication with the influent fluid line and said second portion being shaped to be placed in fluid communication with the port.

3. The connector of claim 2, wherein the first cylindrical portion has a first outer diameter and the second cylindrical portion has a second outer diameter, said first diameter being different from said second diameter.

4. The connector of claim 3, wherein said body has an annular portion dividing said first cylindrical portion and said second cylindrical portion, said annular portion being a circular disk having a hole at its center, said hole being in fluid communication with said spike.

5. The connector of claim 4, wherein said body has at least one scoop cut out of said wall structure at the distal end of said connector.

6. The connector of claim 1, wherein the proximal end of said body has a luer lock.

7. The connector of claim 1, wherein said spike is cylindrical.

8. The connector of claim 7, wherein said spike has a tapered tip.

9. The connector of claim 1, wherein said grip mechanism comprises two grips disposed on opposite sides of said body, each of said grips having a grip lip at one end and a grip handle at the other end.

10. The connector of claim 9, wherein each of said grips is a curved rectangular flap with at least one edge fixed to the body.

11. The connector of claim 10, wherein each of said grips forms a portion of said wall structure.

12. A connector for connecting a fluid line to a port having a receiving end, comprising:

a housing including a wall structure defining an internal cavity, said housing having a proximal end and a distal end, said wall structure at the distal end of said housing having a retaining ring which forms an opening sufficiently large to mate with said port;

a grip mechanism to releasably secure said housing onto said port; and a hollow shaft extending on a center axis of said internal cavity from said proximal end of said housing to a distance not exceeding said distal end of said housing, wherein said hollow shaft and said housing are permanently coupled.

13. The connector of claim 12, wherein said grip mechanism comprises two grip elements disposed on opposite sides of said housing.

14. The connector of claim 12, wherein said retaining ring includes a pair of scoops disposed at opposite sides of said housing.

15. The connector of claim 13, wherein each grip element comprises a grip arm including a proximal end and a distal end, each grip arm having a grip flange at the distal end of said grip arm and each grip arm having a grip handle at the proximal end of said grip arm.

16. A connector for connecting fluid lines equipped with fluid line connectors, comprising:

a housing including a wall structure defining an internal cavity having a center axis, said housing having a proximal end and a distal end, said wall structure of said housing having a lock member which extends into said internal cavity from said wall structure to thereby engage said fluid line connector, said distal end of said connector mating with a fluid line connector; and a cannula extending from said proximal end of said housing along said center axis.

17. The connector of claim 16, wherein said lock member which extends towards said internal cavity comprises a retaining ring.

18. The connector of claim 16, further including means for moving said lock member into and out of engagement with said fluid line connector.

19. The connector of claim 18, wherein said means comprises a lever member connected to said wall structure.

20. The connector of claim 19, wherein said lock member is connected to a flap portion of said wall structure and said lever member is connected to said flap member, whereby engagement of said lever member effectuates movement of said lock member mounted to said flap member.

* * * * *